United States Patent [19]

Kroposki et al.

[11] 4,094,873

[45] June 13, 1978

[54] PROCESS FOR PREPARING PHOSPHOROTHIOATES AND PHENYLPHOSPHONOTHIOATES

[75] Inventors: Lorraine M. Kroposki, Walnut Creek, Calif.; Masao Yoshimine, Midland, Mich.; Harold H. Freedman, Newton Center, Mass.

[73] Assignee: The Dow Chemical Company, Midland, Mich.

[21] Appl. No.: 761,176

[22] Filed: Jan. 21, 1977

Related U.S. Application Data

[60] Division of Ser. No. 600,542, Jul. 31, 1975, Pat. No. 4,028,439, which is a division of Ser. No. 354,040, Apr. 24, 1973, Pat. No. 3,917,621, which is a continuation-in-part of Ser. No. 229,171, Feb. 24, 1972, abandoned.

[51] Int. Cl.$^2$ .................... C07F 9/09; C07F 9/165
[52] U.S. Cl. ........................ 544/243; 260/294.8 K; 260/973; 544/337
[58] Field of Search ............... 260/929, 964, 250 BP, 260/251 P

[56] References Cited

U.S. PATENT DOCUMENTS

| | | | |
|---|---|---|---|
| 3,244,586 | 4/1966 | Rigterink | 167/33 |
| 3,792,132 | 2/1974 | Bernhart | 260/964 |
| 3,917,621 | 11/1975 | Kroposki et al. | 260/294.8 K |
| 3,972,887 | 8/1976 | Freedman | 260/250 BP |
| 4,016,225 | 4/1977 | Kroposki et al. | 260/973 |
| 4,028,439 | 6/1977 | Kroposki et al. | 260/973 |

*Primary Examiner*—Jose Tovar
*Attorney, Agent, or Firm*—L. Wayne White

[57] ABSTRACT

Mixtures of (1) a quaternary ammonium salt(s) and (2) a diazole are novel catalysts in the process of reacting an alkali metal phenate, pyridinate or pyrimidinate with an O,O-dialkyl phosphorochloridothioate or O-alkyl phenylphosphonochloridothioate to produce the corresponding title compounds. The process is conducted under alkaline conditions in a liquid reaction medium. As an example, O,O-diethyl O-(3,5,6-trichloro-2-pyridyl)phosphorothioate is prepared in excellent yields and purity by reacting sodium 3,5,6-trichloro-2-pyridinate with O,O-diethyl phosphorochloridothioate in a stirred methylene chloride-water reaction medium in the presence of a catalytic amount of benzyltriethylammonium chloride and 1-methylimidazole.

17 Claims, No Drawings

PROCESS FOR PREPARING PHOSPHOROTHIOATES AND PHENYLPHOSPHONOTHIOATES

CROSS-REFERENCE TO RELATED APPLICATION

This is a division of application Ser. No. 600,542, filed July 31, 1975, now U.S. Pat. No. 4,028,439 grant 6/7/77, which in turn is a division of Ser. No. 354,040, filed Apr. 24, 1973, now U.S. Pat. No. 3,917,621 granted 11/4/75, which in turn is a continuation-in-part of application Ser. No. 229,171, filed Feb. 24, 1972, now abandoned.

BACKGROUND OF THE INVENTION

The O-pyridyl phosphates and phosphorothioates were described by Rigterink in U.S. Pat. No. 3,244,586. Such compounds are particularly useful as insecticides and biocides. They are represented by Formula I

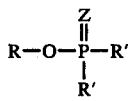     (I)

wherein R represents halopyridyl, Z represents oxygen or sulfur and each R' independently represents lower alkyloxy, amino or lower alkylamino. Rigterink disclosed several methods for preparing the compounds but his preferred method comprised reacting a phosphorochloridate or phosphorochloridothioate of Formula (II)

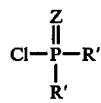     (II)

with an alkali metal or tertiary amine salt of a halopyridinol having the formula R-O-alkali metal or R-OH·tertiary amine. The disclosed methods were carried out in an inert organic liquid under anhydrous conditions. In each of the disclosed processes an alkali metal chloride or the tertiary amine hydrochloride salt is produced as a reaction by-product which is removed by filtration. The disclosure of U.S. Pat. No. 3,244,586 is incorporated herein by reference.

Other phosphorothioates and phenylphosphonothioates have been similarly prepared and used. See, for example, the articles by O. Johnson in Chemical Week, pages 18-46 (26 July 1972) and by E. E. Kenaga and W. E. Allison in the Bulletin of the Entomological Society of America, Vol. 15, No. 2, pages 85-148 (June, 1969) which list many commercially available phosphorothioates and phenylphosphonothioates and which include U.S. patents pertaining to such compounds.

The phosphorothioates and phenylphosphonothioates referred to above and herein prepared correspond to the formula

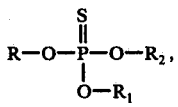     (III)

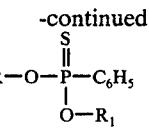     (IV)

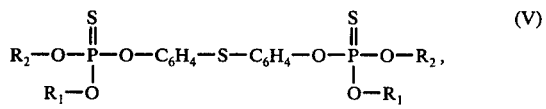     (V)

wherein $R_1$ and $R_2$ are each independently lower alkyl; and R is

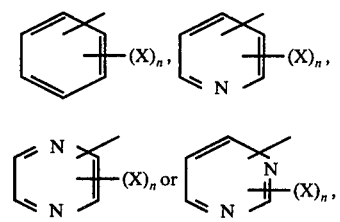

wherein:
n is 0, 1, 2 or 3; and
X is nitro, cyano, halo (fluoro, chloro, bromo and iodo, inclusive), lower alkyl, lower alkoxy, lower alkylthio or lower alkylsulfinyl, with the proviso that R does not bear more than one nitro group, lower alkylthio group or lower alkylsulfinyl group.

By "lower alkyl" is meant in all instances alkyl of 1 to 4 carbon atoms (i.e. methyl, ethyl, propyl and butyl).

SUMMARY OF THE INVENTION

We have discovered that mixtures of (1) a quaternary ammonium salt(s) and (2) a diazole are novel catalysts in the process comprising reacting by contacting (a) an alkali metal phenate, pyridinate or pyrimidinate with (b) an O,O-dialkyl phosphorochloridothioate or O,O-dialkyl phenylphosphonochloridothioate to produce the corresponding O,O-dialkyl phosphorothioate and phenylphosphonothioates. Our novel two-component catalyst represents a substantial process improvement over the prior art in that the reaction rate is higher and the desired products are obtained in extremely high yields and purity.

The Quaternary Ammonium Salts

Essentially any compound from the known class of quaternary ammonium compounds can be used in the instant invention. Suitable quaternary ammonium salts have a minimum solubility of at least about 1 weight percent in the liquid reaction medium at 25° C., and in the case of a 2-phase reaction medium described below, suitable salts have a minimum solubility of at least about 1 weight percent in both the organic phase and the aqueous phase at 25° C. The ammonium salts can be represented by the formula $R_1'R_2'R_3'R_4'N^{\oplus}A^{\ominus}$ (VI), wherein $R_1'$-$R_4'$ are hydrocarbyl groups (e.g. alkyl, aryl, alkaryl, aralkyl, cycloalkyl, etc.) and $R_1'$ can join with $R_2'$ to form a 5- or 6-membered heterocyclic compound having at least one quaternized nitrogen atom in the ring and may also contain one atom of nitrogen, oxygen or sulfur within the ring. Typically, $R_1'$-$R_4'$ are hydrocarbyl groups of from 1 to about 12 carbon atoms. $A^{\ominus}$ in VI is a neutralizing anion and may be varied to convenience. Chloride and bromide are the preferred anions, but other representative anions include fluoride, iodide, tosylate, acetate, bisulfate, etc. The following compounds are illustrative: tetraalkyl ammonium salts, such as tetramethyl-, tetraethyl-, tetrabutyl-, tetrahexyl-, methyltriethyl-, and trioctylmethyl- and tridecylmethyl-ammonium chlorides, bromides, iodides, bisulfates, tosylates, etc.; aralkylammonium salts, such as tetrabenzylammonium chloride, benzyltrimethyl-, benzyltriethylbenzyltributyl-, and phenethyltrimethylammonium chlorides, bromides, iodides, etc.; arylammonium salts, such as triphenylmethylammonium fluoride, chloride or bromide, N,N,N-trimethylanilinium chloride, N,N,N-triethylanilinium bromide, N,N-diethyl-N-ethylanilinium bisulfate, trimethylnaphthylammonium chloride, p-methylphenyltrimethylammonium chloride or tosylate, etc.; 5- and 6-membered heterocyclic compounds containing at least one quaternized nitrogen atom in the ring, such as N,N,N',N'-tetramethylpiperaziniumdichloride, N-methylpyridinium chloride, N-methylpyridinium chloride, N-hexylpyridinium iodide, 4-pyridyltrimethylammonium iodide, 1-methyl-1-azoniabicyclo[2.2.1]heptane bromide, N,N-dibutylmorpholinium chloride, N-ethylthiazolium chloride, N-butylpyrrolium chloride, etc., and other like compounds.

The Diazoles

Diazoles form a known class of compounds. Diazoles suitable for use in the instant process are imidazoles and pyrazoles of the formulas

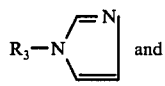 (VI)

and

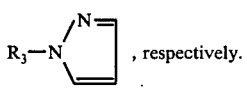 (VII)

, respectively.

In VI and VII, $R_3$ is hydrogen or lower alkyl of from 1 to 6 carbon atoms and is preferably hydrogen, methyl or ethyl and is most preferably methyl. Further, the imidazoles are presently preferred over the pyrazoles. Examples of suitable such diazoles include imidazole, 1-methylimidazole, 1-ethylimidazole, 1-propylimidazole, 1-hexylimidazole, pyrazole, 1-methylpyrazole, 1-ethylpyrazole, 1-butylpyrazole, 1-amylpyrazole and 1-hexylpyrazole, and the like.

The Novel Catalysts

Any combination of quaternary ammonium compound and diazole within the above definitions for such compounds can be used as the catalyst for the above mentioned reaction. However, the preferred catalyst system is a mixture of benzyltrimethylammonium chloride (or bromide) or benzyltriethylammonium chloride (or bromide) and 1-methylimidazole and the most preferred catalyst system is a mixture of benzyltriethylammonium chloride and 1-methylimidazole.

The mole ratio of (1) to (2) can vary from about 1:20 to 20:1, but a mole ratio of about 1:2 to 2:1 is preferred in most instances.

The mixtures of (1) and (2) are used in the process in small but catalytic amounts. For example, amounts from about 0.25 to about 20 mole percent, based on the reactants, are suitable but amounts of from about 0.5 to about 2 mole percent are generally preferred.

Process Parameters

The reaction proceeds at a satisfactory rate at temperatures of from about 0° C. up to about 100° C. with a preferred rate being obtained at temperatures of about 40°-60° C. The reaction pressure is not critical and generally atmospheric or superatmospheric pressures are used as a matter of convenience. Under the above conditions, reaction times of up to 8 hours are common although reaction times of from 0.25 to 5 hours are generally sufficient for the reaction to be substantially complete.

The process is typically conducted in a liquid reaction medium as a convenient means of controlling the reaction temperature. The solvent may be an inert organic liquid such as methylene chloride ($CH_2Cl_2$), chloroform, carbon tetrachloride, benzene, toluene, cyclohexane, and other like chlorinated hydrocarbon solvents and hydrocarbon solvents. Alternatively, the process can be conducted in a two-phase solvent system comprising an inert, water-immiscible, organic liquid and water. The two-phase system is currently preferred because the by-product chloride is washed free from the reaction and is retained in the aqueous phase while the product is retained in the organic phase. A liquid mixture of methylene chloride and water represents the most preferred solvent mixture. The discovery that the process could be conducted in the presence of water without deleteriously affecting the product yield, etc., was most suprising since the phosphorochloridates and phosphorochloridothioates are known to decompose in water. Furthermore, since the pyridinates are water-soluble and the phosphorochloridates and phosphorochloridothioates are essentially water-insoluble, the use of a 2-phase solvent system would have been expected to slow the reaction since contact between the two reactants would be lessened; this effect was not observed.

The process is conducted under neutral or alkaline conditions. Generally the pH of the water phase (when present) is in the range of from about 7 to about 13. Such conditions can be easily achieved by conventional methods, e.g. by conducting the process in the presence of caustic, or other base or by use of an appropriate buffer system.

Agitation (e.g., stirring, swirling, etc.) of the reaction mixture is advantageous, particularly when the process is conducted in the 2-phase liquid reaction medium.

The Reactants

The alkali metal phenates, pyridinates and pyrimidinates are known classes of compounds corresponding to the formulas

 (VIII)

 (IX)

wherein R has the above meaning and M is an alkali metal (Li, Na, K, etc.) but is preferably sodium or potassium and is most preferably sodium.

The O,O-dialkyl phosphorochloridothioates and O-alkyl phenylphosphonochloridothioates are likewise well known classes of compounds which correspond to the formulas

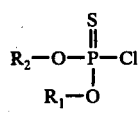 (X)

and

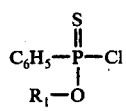 (XI)

wherein $R_1$ and $R_2$ are each independently lower alkyl but are preferably methyl or ethyl.

Various phosphorothioates and phenylphosphonothioates can obviously be prepared by using various combinations of the above reactants. Representative and illustrative lists of suitable reactants and combinations thereof are shown in Tables 1 and 2 below:

Table 1

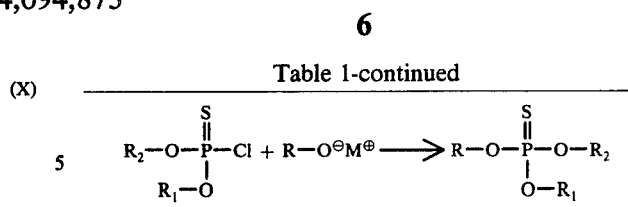

| No. | $R_1$ | $R_2$ | R | M |
|---|---|---|---|---|
| 1 | $CH_3$ | $CH_3$ | 2,3,5-trichloropyridyl | Na |
| 2 | $C_2H_5$ | $C_2H_5$ | 2,3,5-trichloropyridyl | Na |
| 3 | $C_2H_5$ | $C_2H_5$ | 2-fluoropyridyl | Na |
| 4 | $CH_3$ | $CH_3$ | 2,4,5-trichlorophenyl | Na |
| 5 | $C_2H_5$ | $C_2H_5$ | 2,4-dichlorophenyl | K |
| 6 | $CH_3$ | $CH_3$ | 2-chloro-4-iodo-5-chlorophenyl | Na |

Table 1-continued

| No. | $R_1$ | $R_2$ | R | M |
|---|---|---|---|---|
| 7 | $CH_3$ | $CH_3$ | 2-chloro-4-nitrophenyl | Na |
| 8 | $C_2H_5$ | $C_2H_5$ | 4-nitrophenyl | Na |
| 9 | $CH_3$ | $CH_3$ | 4-nitrophenyl | K |
| 10 | $CH_3$ | $CH_3$ | 3-methyl-4-nitrophenyl | K |
| 11 | $CH_3$ | $CH_3$ | 3-methyl-4-(methylthio)phenyl | Na |
| 12 | $C_2H_5$ | $C_2H_5$ | 3-methyl-4-(methylsulfinyl)phenyl | Na |
| 13 | $C_2H_5$ | $C_2H_5$ | 4-(methylsulfinyl)phenyl | Na |
| 14 | $C_2H_5$ | $C_2H_5$ | 2-isopropyl-6-methylpyrimidyl | K |
| 15 | $C_2H_5$ | $C_2H_5$ | pyrimidyl | Na |
| 16 | $CH_3$ | $CH_3$ | 4-cyanophenyl | K |

Table 2

$$C_6H_5-\overset{\overset{S}{\|}}{\underset{R_1-O}{P}}-Cl + R-O^{\ominus}M^{\oplus} \longrightarrow R-O-\overset{\overset{S}{\|}}{\underset{O-R_1}{P}}-O-R_2$$

| | $R_1$ | R | M |
|---|---|---|---|
| 17 | $CH_3$ | Cl-⟨benzene⟩-Br, Cl | Na |
| 18 | $C_2H_5$ | ⟨benzene⟩-$NO_2$ | K |
| 19 | $C_2H_5$ | ⟨benzene⟩-CN | Na |

The compounds of Formula V are prepared in like manner.

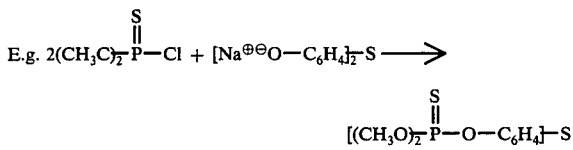

E.g. $2(CH_3O)_2-\overset{\overset{S}{\|}}{P}-Cl + [Na^{\oplus \ominus}O-C_6H_4]_2-S \longrightarrow$ $[(CH_3O)_2-\overset{\overset{S}{\|}}{P}-O-C_6H_4]_2-S$ The following examples further illustrate the invention.

EXAMPLE 1 Preparation of O,O-Dimethyl-0-3,5,6-Trichloro-2-pyridylphosphorothioate To a 3-necked flask, equipped with a stirrer, condenser and a dropping funnel, was added 30 ml. methylene chloride, 74 ml. of water, 3.3 gm. of sodium chloride, 0.38 gm. of sodium hydroxide, 0.7 gm. of boric acid, 0.13 gm. (.56 mmoles) of benzyltriethylammonium chloride and 0.05 gm. (0.56 mmoles) of 1-methylimidazole and 12.5 gm. (56 mmoles) sodium 3,5,6-trichloro-2-pyridinate (NaTCP). The stirred mixture was heated to 35° C. and 9.03 g. (56.3 mmoles) of O,O-dimethylphosphorochloridothioate (DMPCT) was added over a 1 minute period and brought the reaction mixture to reflux (42° C.). The stirred reaction mixture was refluxed for 1.5 hours. The $CH_2Cl_2$ layer was separated and washed with 100 ml. of water. Then the $CH_2Cl_2$ was removed on a rotary evaporator. The product was cooled in an ice water bath to give 17.3 gm. of white crystals of O,O-dimethyl-O-3,5,6-trichloro-2-pyridylphosphorothioate (yield 93.7%).

In like manner the following runs were conducted:

TABLE 2A

| O,O-Dimethyl-O-3,5,6-Trichloro-2-Pyridylphosphorothioate | | | |
|---|---|---|---|
| Benzyltriethylammonium Chloride, Mole % | 1-Methylimidazole Mole % | Time, Hrs. | Yield, %* |
| 1 | 1 | 1.6 | 93.7 |
| 0.75 | 0.75 | 3.8 | 94.9 |
| 0.50 | 0.50 | 4.5 | 94.6 |
| 0.75 | 0.50 | 3.1 | 91.7 |
| — | 1 | 3.5 | 36.5 |
| 1 | — | 23.0 | 40.0 |

*Isolated Yield

EXAMPLE 2 Preparation of O,O-Diethyl-O-3,5,6-Trichloro-2-pyridylphosphorothioate To a 3-necked flask, equipped with a stirrer, condenser and a dropping funnel, was added 30 ml. methylene chloride, 74 ml. of water, 3.5 gm. of sodium chloride, 0.43 gm. of sodium hydroxide, 0.78 gm. of boric acid, 0.14 gm. (0.6 mmole) of benzyltriethylammonium chloride, 0.04 gm. (0.45 mmole) of 1-methylimidazole and 13.2 gm. (60 mmoles) NaTCP. The stirred mixture was heated to 35° C. and 11.3 gms. (60 mmole) of O,O-diethylphosphorochloridothioate (DEPCT) was added over a 1 minute period and brought the reaction mixture to reflux (42° C.). The stirred reaction mixture was refluxed for 3.9 hours. The $CH_2Cl_2$ layer was separated and washed with 100 ml. of water. Then the $CH_2Cl_2$ was removed on a rotary evaporator. The product was cooled in an ice water bath to give 19.41 gm. of white crystals (92.43% yield of product having a purity of 99.5%).

In like manner the following runs were conducted:

Table 3

| O,O-Diethyl-O-3,5,6-Trichloro-2-Pyridylphosphorothioate | | | | |
|---|---|---|---|---|
| Benzyltriethylammonium Chloride, Mole % | I-Methylimidazole, Mole % | Time, Hrs. | Yield, %* | Purity, % |
| 1 | 1 | 2.2 | 97.1 | 98.2 |
| 1 | 0.75 | 3.9 | 92.4 | 99.5 |
| 0.75 | 0.75 | 3.6 | 94.0 | 98.0 |
| 0.75 | 0.50 | 5.1 | 89.0 | 97.1 |
| 0.50 | 0.50 | 3.8 | 95.7 | 97.7 |
| | Imidazole, Mole % | | | |
| 5 | 5 | 7.1 | 94.6 | — |
| | Pyrazole, Mole % | | | |
| 5 | 5 | 28 | 88.5 | — |

*Isolated yield

EXAMPLES 3–8

The following experiments were conducted using substantially the same procedure. In each instance the catalyst used was a mixture of benzyltriethylammonium chloride and 1-methylimidazole. The catalyst level for examples 3–7 was 0.75 mole percent for each catalyst component based on combined starting materials, and was 1.0 mole percent for each catalyst component in example 8. Further, boric acid was included in examples 3–5 (as per examples 1 and 2) but boric acid was not included in examples 6–8. The experimental results are summarized in Table 4.

Table 4

| Ex. | Reactants | Product | Reaction Time (Hrs.) | Conversion* (%) | Yield** (%) | Product Description |
|---|---|---|---|---|---|---|
| 3 | DMPCT + Na⊕⊖O—⟨⟩—SCH₃ → (CH₃O)₂P(S)—O—⟨⟩—SCH₃ (with CH₃ substituents) | | 2.5 | 100 | 95.4 | Red oil |
| 4 | C₆H₅—P(S)—Cl + CH₃—O, Na⊕⊖O—⟨⟩—Br → C₆H₅—P(S)—O—⟨⟩—Br (with Cl substituents, CH₃O) | | 2.5 | 78.1 | 95.4 | White Solid |
| 5 | DMPCT + Na⊕⊖O—⟨⟩—NO₂ → (CH₃O)₂P(S)—O—⟨⟩—NO₂ (with CH₃ substituents) | | 3 | 100 | ca.100 | Brown liquid |
| 6 | DEPCT + Na⊕O⊖—⟨pyrazine⟩ → (C₂H₃—O)₂P(S)—O—⟨pyrazine⟩ | 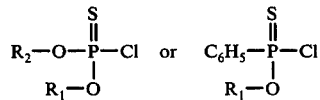 | 7 | Not Measured | 82 | |
| 7 | DEPCT + Na⊕⊖O—⟨pyridine-F⟩ → (C₂H₅O)₂P(S)—O—⟨pyridine-F⟩ | 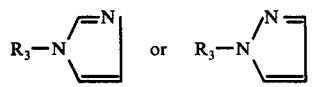 | 6 | Not measured | 86 | |
| 8 | DMPCT + Na ⊕⊖ ⟨⟩—Cl → (CH₃O)₂P(S)—O—⟨⟩—Cl (with Cl substituents) |  | 1 | 100 | 92 | |

*Based on conversion of phenate, pyridimate or pyrimidinate reactant (100% assumed for Ex. 6 and 7).
**Percent yield is based on material converted.

Those skilled in the art will recognize that the above examples are merely illustrative and that other novel catalyst mixtures could be used as described above. Additionally, they will recognize that compounds could be similarly prepared by using various combinations of reactants as described above.

We claim:

1. In the process of preparing a compound corresponding to the formula $$R-O-\overset{\overset{S}{\|}}{\underset{O-R_1}{P}}-O-R_2, \quad R-O-\overset{\overset{S}{\|}}{\underset{O-R_1}{P}}-C_6H_5 \text{ or}$$

$$R_2-O-\overset{\overset{S}{\|}}{\underset{R_1-O}{P}}-O-C_6H_4-S-C_6H_4-O-\overset{\overset{S}{\|}}{\underset{O-R_1}{P}}-O-R_2,$$

wherein:

$R_1$ and $R_2$ are each independently lower alkyl; and

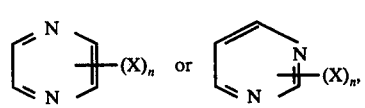

wherein:

$n$ is 0, 1, 2 or 3; and

X is nitro, cyano, halo, lower alkyl, lower alkoxy, lower alkylthio or lower alkylsulfinyl, with the proviso that R does not bear more than one nitro group, lower alkylthio group or lower alkylsulfinyl group; by reacting in an inert liquid reaction medium and under neutral or alkaline conditions (a) a compound corresponding to the formula $$R-O^{\ominus}M^{\oplus} \text{ or } M^{\oplus \ominus}O-C_6H_4-S-C_6H_4-O^{\ominus}M^{\oplus}$$

with (b) a compound corresponding to the formula $$R_2-O-\overset{\overset{S}{\|}}{\underset{R_1-O}{P}}-Cl \quad \text{or} \quad C_6H_5-\overset{\overset{S}{\|}}{\underset{R_1-O}{P}}-Cl$$

wherein M is an alkali metal and R, $R_1$ and $R_2$ have the aforesaid meaning;

the improvement consisting of conducting the process in the presence of a small but catalytic amount of (1) a quaternary ammonium salt having a minimum solubility of at least 1 weight percent in the liquid reaction medium at 25° C and (2) a diazole corresponding to the formula

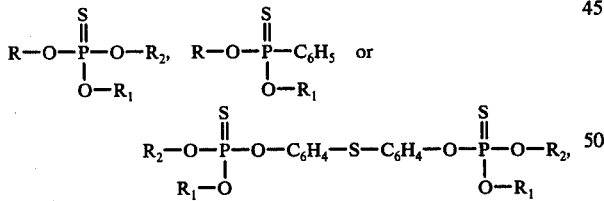

wherein $R_3$ is hydrogen or alkyl of 1 to 6 carbon atoms.

2. The process defined in claim 1 wherein (1) is an ammonium salt of the formula $$R_1'R_2'R_3'R_4'N^{\oplus}A^{\ominus}$$

wherein $R_1'$-$R_4'$ are each independently hydrocarbyl groups of from 1 to about 12 carbon atoms, or $R_1'$ is joined with $R_2'$ to form a 5- or 6-membered heterocyclic having at least one quaternized nitrogen atom within the ring and may additionally contain one non-adjacent atom of nitrogen, oxygen or sulfur within the ring; and $A^\ominus$ is a neutralizing anion.

3. The process defined in claim 2 wherein (1) is benzyltrimethylammonium chloride or bromide, or benzyltriethylammonium chloride or bromide.

4. The process defined in claim 3 wherein (1) is benzyltriethylammonium chloride.

5. The process defined in claim 1 wherein (2) is

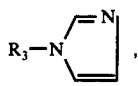

wherein $R_3$ has the aforesaid meaning.

6. The process defined in claim 1 wherein $R_3$ is hydrogen, methyl or ethyl.

7. The process defined in claim 6 wherein $R_3$ is methyl.

8. The process defined in claim 1 wherein the mole ratio of (1) to (2) is from about 1:20 to about 20:1.

9. The process defined in claim 8 wherein said ratio is from about 1:2 to about 2:1.

10. The process defined in claim 1 wherein the combined amount of (1) and (2) is from about 0.25 to about 20 mole percent, based on the combined moles of (a) and (b).

11. The process defined in claim 10 wherein the combined amount of (1) and (2) is from about 0.5 to about 2 mole percent.

12. The process defined in claim 1 wherein said process is conducted in an agitated 2-phase solvent system consisting of an inert water-immiscible organic liquid and water.

13. The process defined in claim 1 wherein $R_1$ and $R_2$ are methyl or ethyl.

14. The process defined in claim 13 wherein R is

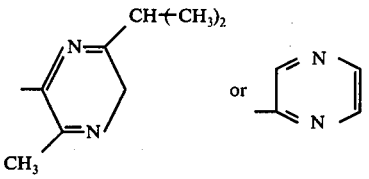

15. The process defined in claim 14 wherein (1) is benzyltrimethylammonium chloride or bromide or benzyltriethylammonium chloride or bromide.

16. The process defined in claim 15 wherein (2) is

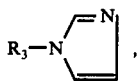

wherein $R_3$ is hydrogen methyl or ethyl.

17. The process defined in claim 16 wherein said process is conducted in an agitated 2-phase solvent system consisting of an inert water-immiscible organic liquid and water.

* * * * *